United States Patent
Redkey

(10) Patent No.: US 11,013,558 B2
(45) Date of Patent: May 25, 2021

(54) METHOD AND APPARATUS FOR ENDO FISTULA LASER THERAPY

(71) Applicant: H. Christopher Redkey, Westminster, MA (US)

(72) Inventor: H. Christopher Redkey, Westminster, MA (US)

( * ) Notice: Subject to any disclaimer, the term of this patent is extended or adjusted under 35 U.S.C. 154(b) by 0 days.

(21) Appl. No.: 16/285,357

(22) Filed: Feb. 26, 2019

(65) Prior Publication Data

US 2019/0262073 A1    Aug. 29, 2019

Related U.S. Application Data

(60) Provisional application No. 62/635,914, filed on Feb. 27, 2018.

(51) Int. Cl.
  *A61B 18/22* (2006.01)
  *A61B 17/00* (2006.01)
  *A61B 18/00* (2006.01)

(52) U.S. Cl.
  CPC .......... *A61B 18/22* (2013.01); *A61B 17/0057* (2013.01); *A61B 2017/00641* (2013.01); *A61B 2017/00663* (2013.01); *A61B 2018/005* (2013.01); *A61B 2018/00577* (2013.01); *A61B 2018/00625* (2013.01)

(58) Field of Classification Search
  CPC ................ A61B 18/22; A61B 17/0057; A61B 2017/00663; A61B 2017/00641; A61B 2018/00625; A61B 2018/00577; A61B 2018/005
  See application file for complete search history.

(56) References Cited

U.S. PATENT DOCUMENTS

| | | | |
|---|---|---|---|
| 5,312,399 | A | 5/1994 | Hakky et al. |
| 5,458,595 | A | 10/1995 | Tadir et al. |
| 5,628,762 | A | 5/1997 | Al-Tameem |
| 7,549,424 | B2 | 6/2009 | Desai |
| 8,709,057 | B2 | 4/2014 | Tettamanti et al. |
| 8,936,592 | B2 | 1/2015 | Beck et al. |
| 2011/0282334 | A1 | 11/2011 | Groenhoff |
| 2012/0004546 | A1 | 1/2012 | Neuberger et al. |

*Primary Examiner* — Rex R Holmes
(74) *Attorney, Agent, or Firm* — Maine Cernota & Rardin; Walter F. Dawson, Esq.

(57) ABSTRACT

A method and apparatus for rectal fistula laser treatment wherein an insertion tube of a coupler is inserted into a fistula from proximal to distal end. The insertion tube is then purged using sterile water and/or air. A flexible optical waveguide is then inserted through the coupler including the insertion tube until the end of the optical waveguide protrudes 1-3 mm from the distal end of the insertion tube. The optical waveguide is secured to the coupler by a lock nut of the coupler. The insertion tube locked to the optical waveguide is withdrawn through the fistula while CO2 laser radiation is passed down the optical waveguide so that laser radiation is delivered to the inner wall of the fistula at a specific rate as the laser radiation treats the fistula.

15 Claims, 5 Drawing Sheets

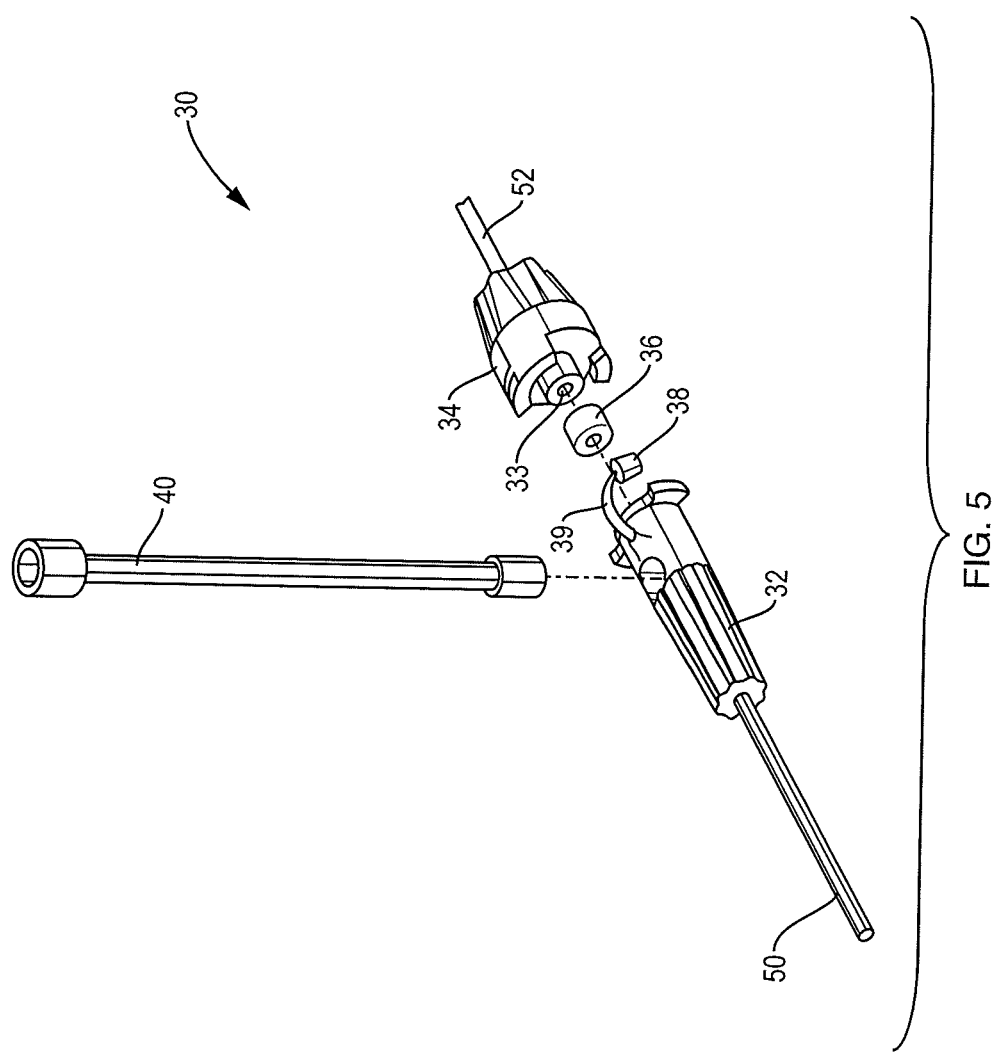

METHOD AND APPARATUS FOR ENDO FISTULA LASER THERAPY

CROSS-REFERENCE TO RELATED APPLICATION

This is a Nonprovisional patent application claiming priority of Provisional Application for Patent No. 62/635,914, filed Feb. 27, 2018, the complete subject matter of which is incorporated herein by reference in its entirety.

BACKGROUND OF THE INVENTION

Field of the Invention

The present invention relates generally to treatment of rectal fistula in normal, Crohns and IBS patients, to an improved method using $CO_2$ laser, more efficient and flexible waveguide and coupling device that targets the $H_2O$ chromophore in tissues thereby vaporizing and ablating more efficiently without any surgical cutting to promote healing and closure of fistula.

Description of Related Art

In certain invasive medical procedures thermal or other energy is administered to a patient with beneficial effects. For example, energy can be used to detect a tumor or a region of the body, or to destroy or denature diseased or malfunctioning body tissue. One example of this type of treatment is disclosed in U.S. Pat. No. 6,095,149, issued Aug. 1, 2000, which describes the treatment of in-verbal disc abnormalities with thermal energy.

U.S. Pat. No. 5,628,762 issued May 12, 1007 to Moshin Al-Tameen discloses a method of using a device having a cutting tool for excising a fistula track and also discloses a laser emitting device to dissect the fistula track from surrounding tissue. However, this prior art does not disclose the simplified structure and improved results of the present invention.

U.S. Patent Application Publication No. 2011/0282334 discloses a device and method for fistula treatment comprising a laser source, fiber optics device and an imaging system. Radiation is delivered to fistula until shrinkage and closure are observed. However, the waveguide elements of the present invention are not disclosed.

BRIEF DESCRIPTION OF THE DRAWINGS

The appended claims particularly point out and distinctly claim the subject matter of this invention. The various objects, advantages and novel features of this invention will be more fully apparent from a reading of the following detailed description in conjunction with the accompanying drawings in which like reference numerals refer to like parts and, in which:

FIG. 5 is an exploded perspective view of the coupler having a flexible insertion tube extending at one end and a removable lock nut at the other end.

SUMMARY OF THE INVENTION

Figure 1:
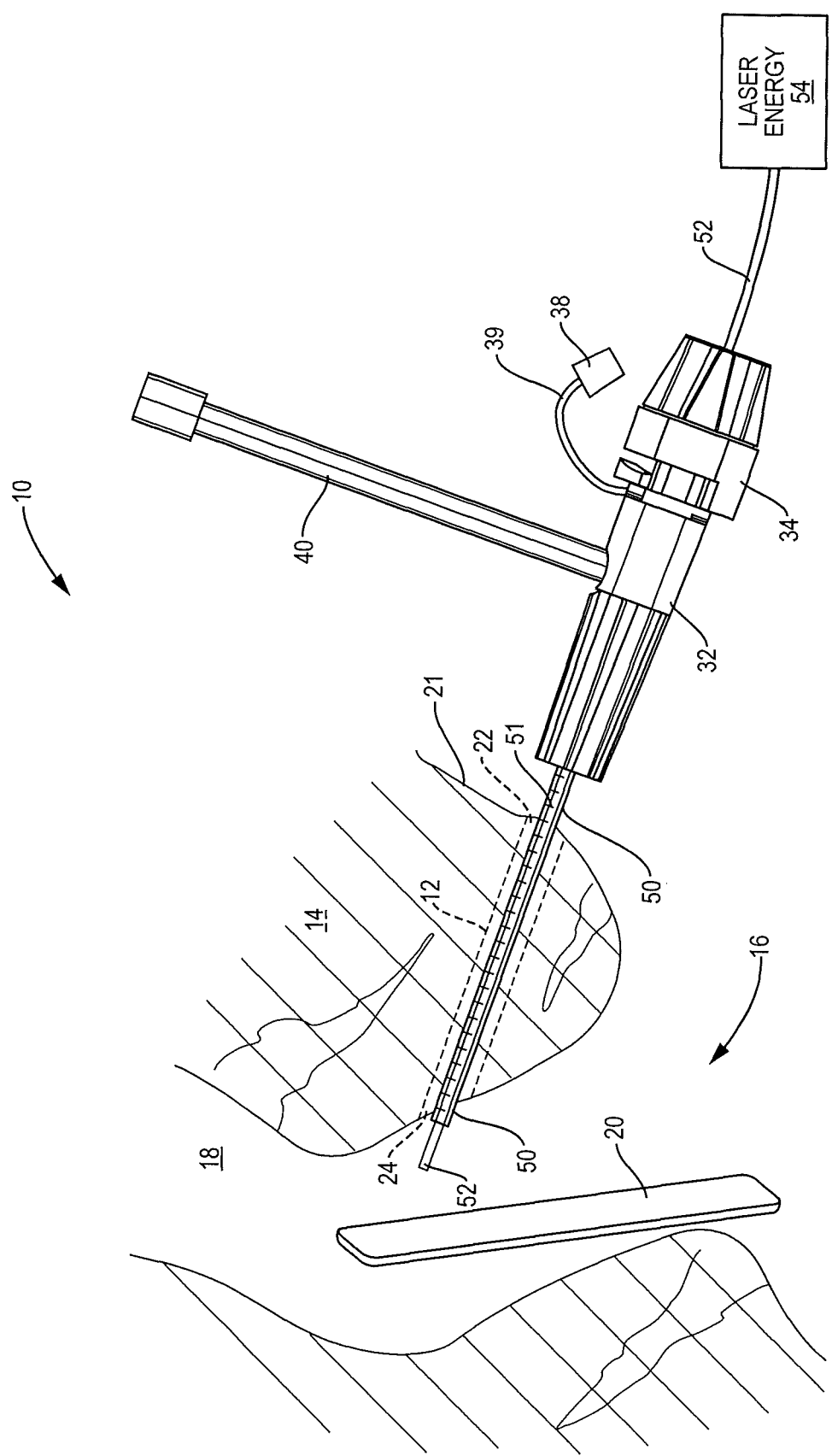
FIG. 1 depicts a diagram of a preferred embodiment of the present invention for performing rectal fistula laser treatment.

Accordingly, it is therefore an object of this invention to provide a more efficient and flexible method and apparatus for performing endo fistula laser treatment with a $CO_2$ laser that treats the targeted tissue more efficiently resulting in less treatment time, better tissue ablation and no or reduced recurrence.

It is another object of this invention to vaporize and ablate more efficiently unwanted fistula tissue due to tissue absorption coefficient characteristics at the laser wavelength of approximately 10.6 microns wherein the $CO_2$ laser light targets the $H_2O$ chromophone in the tissue to be treated.

It is a further object of this invention to provide less collateral trauma into surrounding tissues using the method and apparatus of this invention.

These and other objects are accomplished by a method of providing laser therapy to a fistula of a patient comprising the steps of (a) preparing the patient rectal fistula site and inserting a line such as a surgical silk line into said fistula until the line extends into and exits from an anal canal of the patient, (b) inserting an insertion tube extending from a first end of a coupler into the fistula extending from a coupler into the fistula using said line as a guide and removing the line after the insertion tube is positioned within the fistula, (c) purging the insertion tube using a purge tube attached to the coupler to remove any tissue or debris, (d) inserting a waveguide into the coupler including the insertion tube, the insertion tube being positioned within the fistula, (e) locking the waveguide to the insertion tube end of the coupler using a lock nut of the coupler and (f) applying laser energy via the waveguide to the fistula and slowly removing the locked together insertion tube/waveguide through the fistula at a predetermined rate.

The step of purging the insertion tube positioned within the fistula comprises the step of inserting at least one of sterile water and forced air into the purging tube. The step of inserting an optical waveguide into the coupler including the insertion tube, the insertion tube being positioned within the fistula, further comprises the step of exposing the waveguide in the range of 1-3 mm from a distal end of the insertion tube.

The method comprises the step of inserting a beam block into the anal canal of the patient opposite a distal end of the waveguide extending from the insertion tube positioned in the fistula of the patient. The step of applying laser energy via the waveguide comprises the step of providing laser dosimetry in the range of approximately 15 watts and slowly removing from the fistula the locked together insertion tube/waveguide at a rate of approximately 1 mm per second. The method further comprises the step of suturing an internal distal opening of the fistula in the anal canal.

Additional objects, features and advantages of the invention will become apparent to those skilled in the art upon consideration of the following detailed description of the preferred embodiment exemplifying the best mode of carrying out the invention as presently perceived.

DESCRIPTION OF PREFERRED EMBODIMENT

Referring to FIG. 1, a method and apparatus for performing endo fistula laser therapy 10 is shown. As is well-known a fistula 12 is an abnormal passage or infected tunnel that develops between a hollow organ such as an anal canal 18 and a body skin or surface 21. FIG. 1 shows an improved method 10 for treating the fistula 12, a distal end of which extends from the anal canal 18 through a patient tissue or buttocks 14 to a proximal end at the body skin 21.

The method 10 includes the use of laser energy provided by a CO2 laser 54 having an optical waveguide 52 for delivering the laser energy for treating the fistula 12. The tip of the optical waveguide 52 could cause trauma to good soft tissue, so for some invasive applications, it is not desirable to insert the optical waveguide 52 directly into body tissue. Instead, the optical waveguide 52 is inserted into a flexible insertion tube 50 which extends from a coupler 30, as shown in FIG. 5, and also includes a locking nut 34, a cap 38 and a purge tube 40. Furthermore, to protect good tissue, a beam block 20 is inserted into the anal canal 18 and positioned opposite a distal end of the optical waveguide 52.

Figure 2:
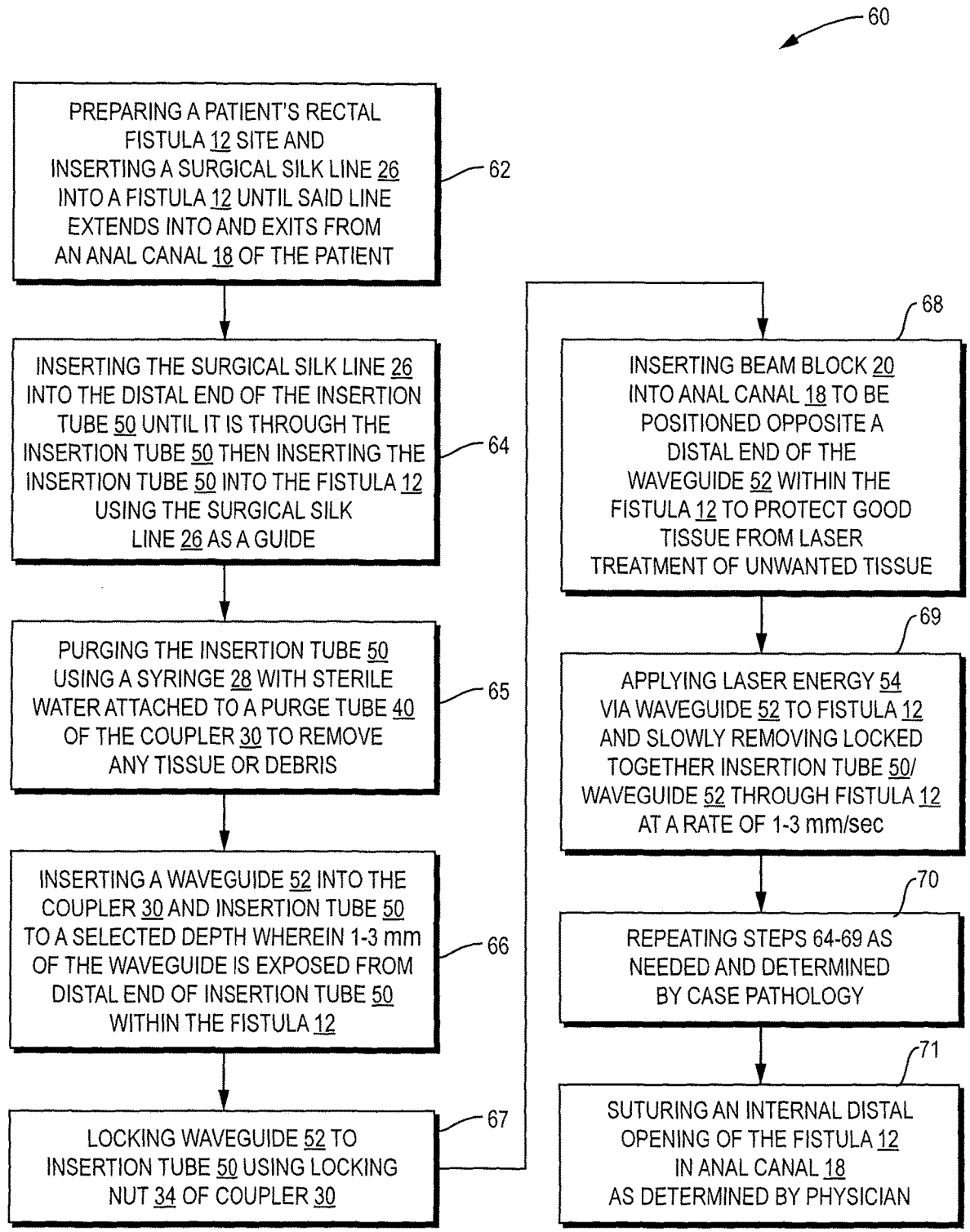
FIG. 2 is a block diagram of the steps of the method for performing fistula laser therapy according to the present invention.
Figure 3:
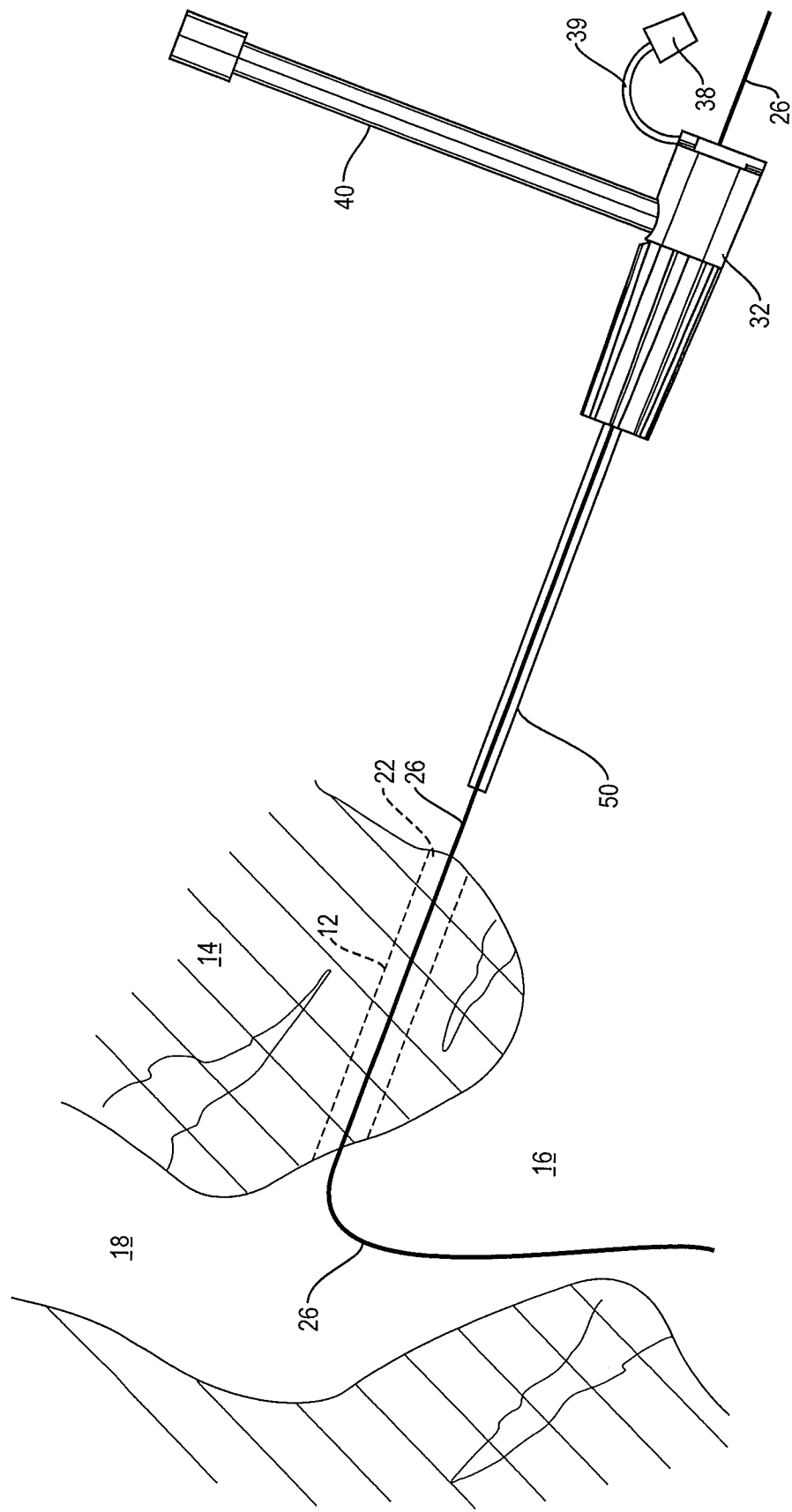
FIG. 3 illustrates the step of the method of inserting a surgical silk line into a fistula site for guiding the insertion of an insertion tube into the fistula.

FIG. 2 shows a block diagram 60 of the steps of the method for performing the endo fistula laser therapy for the fistula 12 as shown in FIG. 1 and the steps are further described as follows:

Step 62 is preparing a patient's rectal fistula 12 site which includes cleaning and site preparation according to generally accepted medical practice methods. Also Step 62 includes inserting a surgical silk line 26 (or a line of similar characteristics) into the fistula 12 from proximal end 22 to distal end 24 and then the surgical silk line exits the anal canal 18 of the patient.

The next Step 64 includes inserting the surgical silk line 26 into the distal end of the insertion tube 50 until it extends through the insertion tube 50 then inserting the insertion tube 50 into the fistula 12 using the surgical silk line 26 as a guide. The surgical silk line 26 is removed after the insertion tube 50 is positioned in the fistula 12.

Figure 4:
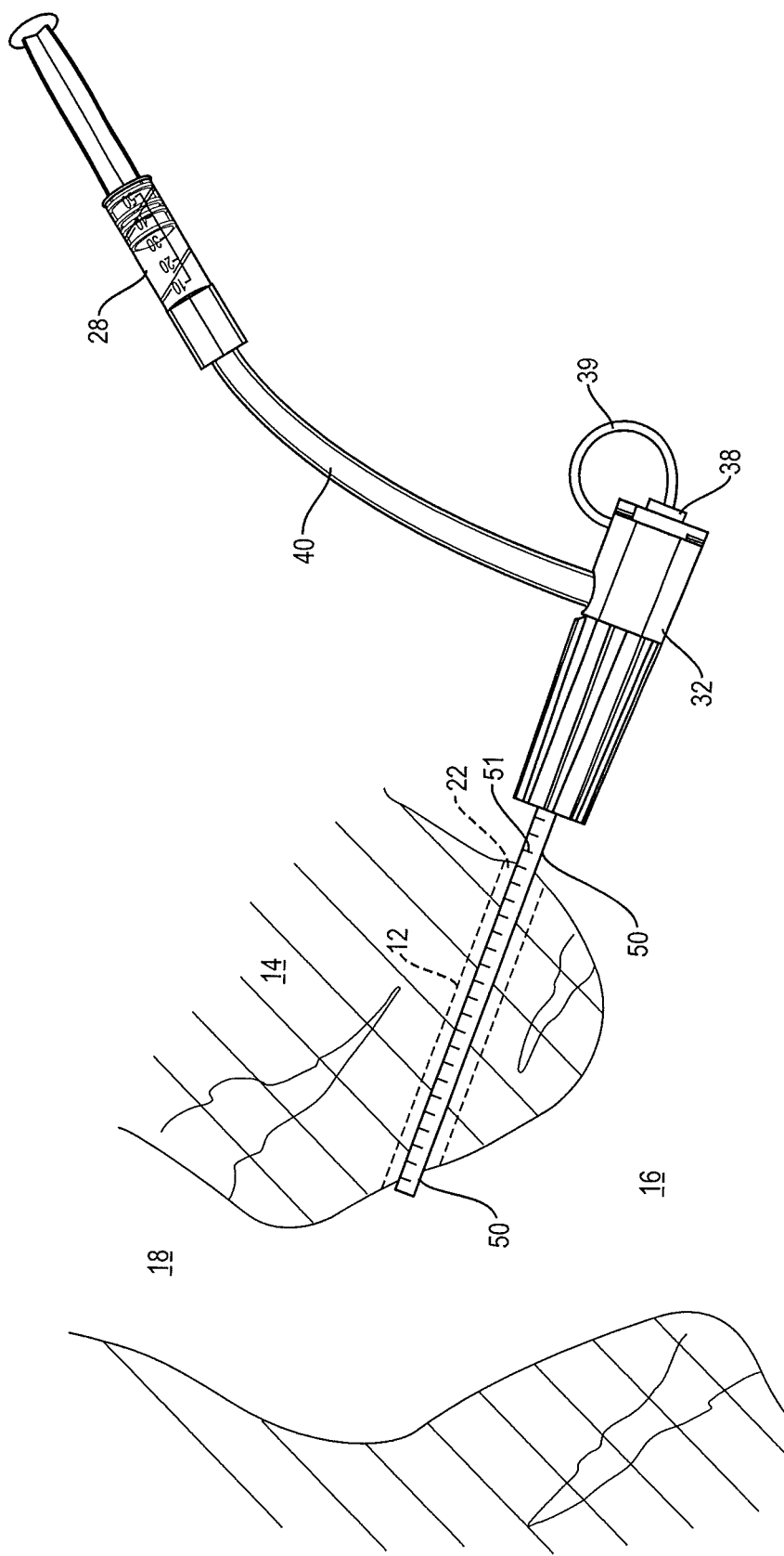
FIG. 4 illustrates the step of the method of using a purge tube of a coupler to provide sterile water held in a syringe for purging the insertion tube to remove any tissue or debris.

Step 65 is illustrated in FIG. 4 and includes purging the insertion tube 50 before inserting a waveguide 52 using a syringe 28, containing sterile water, which is attached to the purge tube 40 of the coupler 30 to remove any tissue or debris via the anal canal 18. Prior to injecting the sterile water, a cap 38 of the coupler 30 is inserted into an open end of the coupler 30 when the lock nut 34 is removed. As an alternative to sterile water, air under pressure may be used to remove any tissue or debris.

Step 66 consists of inserting the optical waveguide 52 extending from a CO2 laser 54 into the coupler 30 (with the locking nut unlocked) and through the insertion tube 50 to a selected depth wherein 1-3 mm of the waveguide 52 is exposed from the distal end of the insertion tube positioned within the fistula 12 as shown in FIG. 1.

Step 67 is locking together the waveguide 52 to the insertion tube 50 by tightening the locking nut 34 of the coupler 30 to secure the waveguide within the coupler 30 by means of a compression washer 36 of the coupler 30.

Step 68 consists of inserting a beam block 20 into the anal canal 18 to be positioned opposite a distal end of the waveguide 52 within the fistula 12 to protect good tissue from laser treatment of unwanted tissue. Now that the insertion tube 50 and the waveguide 52 are secured in position within the fistula 12 and the beam block 20 is inserted, the CO2 laser 54 is set to standby with approximately 15 watts of power to be delivered to the fistula tissue. The CO2 laser may be embodied by Model No. MD 30 ULTRA, Manufactured by LEI (Laser Engineering, Inc.) of Nashville, Tenn.

Step 69 is applying the laser energy via the waveguide 52 to fistula 12 in a continuous or repetitive manner. Laser radiation is delivered to the inner wall of the fistula 12 and the radiation is absorbed and thermally restructures the walls of the fistula 12. The insertion tube 50 has graduated markings 51 for assisting a surgeon to withdraw the secured together insertion tube 50/waveguide 52 at a desired rate which in this method is a distance per unit of time. The insertion tube 50 and the optical waveguide 52 which are secured together are slowly removed from the fistula 12 at a rate of approximately 1 mm per second while a laser energy dose at approximately 15 watts is emitted from the distal end of the optical waveguide 52. A preferred radiation wavelength is 10.6 microns. Alternate sources of laser energy include the use of a Thulium Yag laser at a wavelength of 2 microns or 10.6 microns and an Erbium: Yag laser at a wavelength of 2.9 microns.

When the secured together insertion tube 50/waveguide 52 reach the proximal end 22 of the fistula 12, the CO2 laser energy is ceased. A visual and/or audible indicator may be provided to give an indication of how fast the insertion tube 50/waveguide 52 is withdrawn. The withdrawal rate is determined by the surgeon and the pathology of the fistula 12.

The CO2 wavelength of 10.6 microns is readily absorbed by $H_2O$. With the understanding that the human body is comprised of 70+ percent water ($H_2O$) it is understood that tissue absorption at this wavelength is high. The tissue readily absorbs the light which subsequently causes the $H_2O$ chromophore in the cells to increase its energy level to a vaporization event. The target tissue mainly infected muscle, epithelial, fat, scar and collagen are readily vaporized with the incidence of the 10.6—micron energy at determined energy levels. The ablation of this infected tissue and the subsequent destruction of the resident infected cells promotes the patient's body to heal the fistula properly.

Step 70 is where the surgeon decides repeating steps 64-69 as needed depending on the patient case pathology. When laser energy treatment of the fistula is ended, Step 71 provides suturing of an internal distal end opening 24 of the fistula 12 in the anal canal 18. However, the Physician may determine that the internal opening is not suturable.

Referring now to FIG. 5, an exploded perspective view of the coupler 30 shows the flexible insertion tube 50 extending away from and forming a first end of the coupler 30 and a removable lock nut 34 forming a second end of the coupler 30. The insertion tube 50 may be molded or glued within the coupler 30. A flexible purge tube 40 extends from a side 32 of the coupler 30 and is approximately six inches long and connects to the syringe 28 as shown in FIG. 4 during the fistula purge step 65. Through the center of the coupler 30 is a cylindrical cavity 33 for receiving the waveguide 52, and the waveguide 52 passes through the coupler 30 including the insertion tube 50. A cap 38 is attached at the end of a flexible plastic cord 39 which extends from the surface of the coupler 30. The cap cord 39 is long enough for the cap 38 to be inserted into the open end of the coupler 30 when the lock nut 34 is removed, such as during the purging step 65. The diameter of the cap 38 is approximately 1.5 mm ID and 3-4 mm OD). The coupler 30 has a compression washer 36 so that when the lock nut 34 is attached, the waveguide 52 within the coupler 30, becomes secured to the coupler 30, and the waveguide 52 cannot move inside the coupler 30 including the insertion tube 50. The lock nut 34 compress or squeezes the washer 36 to a level of gripping the waveguide 52 sufficiently to lock it in place.

The insertion tube 50 has an inside diameter of approximately 1.5-2 mm which is sufficient for the waveguide to pass within. It is made of a flexible plastic/polyethylene tube approximately 10-15 cm long with an outside diameter of approximately 1.7-2.2 mm. The insertion tube 50 has external graduated markings 51 in 1 mm increments for use during the withdrawal dosimetry monitoring of the waveguide 52 which is locked to the insertion tube 50 during the application of laser energy. The coupler 30 which includes insertion tube 50 integrated into one end may be obtained from G-Tech, Inc. of Westminster, Mass.

This invention has been disclosed in terms of a certain embodiment. It will be apparent that many modifications can be made to the disclosed method and apparatus for endo fistula laser therapy without departing from the invention. Therefore, it is the intent of the appended claims to cover all such variations and modifications as come within the true spirit and scope of this invention.

What is claimed is:

1. A method of providing laser therapy to a fistula of a patient comprising the steps of:
    (a) preparing a site of said fistula and inserting a line into said fistula until said line extends into and exits from an anal canal of said patient;
    (b) inserting an insertion tube extending from a first end of a coupler into said fistula using said line as a guide and removing said line after said insertion tube is positioned within said fistula;
    (c) purging said insertion tube using a purge tube attached to said coupler to remove any tissue or debris;
    (d) inserting a waveguide into said coupler including said insertion tube, said insertion tube being positioned within said fistula;
    (e) locking said waveguide to said insertion tube end of the coupler using a lock nut of said coupler; and
    (f) applying laser energy via said waveguide to said fistula and slowly removing said locked together insertion tube and waveguide through said fistula at a predetermined rate.

2. The method as recited in claim 1 wherein said step of using said line as said guide for inserting said insertion tube into said fistula comprises the step of using a surgical silk line.

3. The method as recited in claim 1 wherein said step of purging said insertion tube positioned within said fistula comprises the step of inserting at least one of sterile water and air into said purging tube.

4. The method as recited in claim 1 wherein said step of inserting said waveguide into said coupler including said insertion tube, said insertion tube being positioned within said fistula, further comprises the step of exposing said waveguide in the range of 1-3 mm from a distal end of said insertion tube.

5. The method as recited in claim 1 wherein said step of inserting said waveguide into said coupler including said insertion tube comprises the step of providing an optical waveguide.

6. The method as recited in claim 1 wherein said method comprises the step of inserting a beam block into said anal canal of said patient opposite a distal end of said waveguide extending from said insertion tube positioned in said fistula of said patient.

7. The method as recited in claim 1 wherein said step of applying laser energy via said waveguide comprises the step of providing laser dosimetry in the range of approximately 15 watts and slowly removing from said fistula said locked together insertion tube and waveguide at said predetermined rate of approximately 1 mm per second.

8. The method as recited in claim 1 comprises the step of repeating steps (b) to (f) as needed and determined by case pathology.

9. The method as recited in claim 1 comprises the step of suturing an internal distal opening of said fistula in said anal canal.

10. A method for providing laser therapy to a fistula of a patient comprising the steps of:
    (a) inserting a line into said fistula until said line extends into and exits from an anal canal of said patient;
    (b) inserting means for receiving a waveguide into said fistula using said line as a guide and removing said line after said means for receiving a waveguide is positioned within said fistula;
    (c) purging said means for receiving a waveguide using a purge tube attached to said waveguide receiving means;
    (d) inserting a waveguide into said waveguide receiving means until said waveguide extends beyond a distal end of said waveguide receiving means;
    (e) locking said waveguide to said waveguide receiving means using means for locking provided by said waveguide receiving means; and
    (f) applying laser energy via said waveguide to said fistula and slowly removing at a predetermined rate said locked together waveguide and said waveguide receiving means from said fistula.

11. The method as recited in claim 10 wherein said step of inserting a waveguide into said means for receiving a waveguide positioned within said fistula, further comprises the step of exposing said waveguide in a range of 1-3 mm from said distal end of said waveguide receiving means.

12. The method as recited in claim 10 wherein said method further comprises the step of inserting into said anal canal, means for blocking said laser energy entering said anal canal of said patient opposite a distal end of said waveguide extending from said means for receiving a waveguide positioned within said fistula of said patient.

13. The method as recited in claim 10 wherein said step of applying laser energy via said waveguide comprises a step of providing laser dosimetry in the range of approximately 15 watts and slowly removing from said fistula said locked together waveguide receiving means and said waveguide.

14. The method as recited in claim 10 comprises the step of repeating steps (a) to (f) as needed to destroy infected tissue of said fistula as determined by case pathology.

15. The method as recited in claim 10 wherein said step of inserting said waveguide into said means for receiving a waveguide comprises the step of inserting an optical waveguide.

* * * * *